(12) United States Patent
Ditt et al.

(10) Patent No.: US 8,194,962 B2
(45) Date of Patent: Jun. 5, 2012

(54) METHOD FOR DETECTING MOVEMENTS AND CORRECTING MOVEMENTS IN TOMOGRAPHIC AND PROJECTIVE IMAGE SERIES AND TOMOGRAPHY OR PROJECTION SYSTEM FOR IMPLEMENTING THIS METHOD

(75) Inventors: Hendrik Ditt, Nürnberg (DE); Grzegorz Soza, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 929 days.

(21) Appl. No.: 12/232,596

(22) Filed: Sep. 19, 2008

(65) Prior Publication Data

US 2009/0092305 A1 Apr. 9, 2009

(30) Foreign Application Priority Data

Sep. 27, 2007 (DE) .......................... 10 2007 046 579

(51) Int. Cl.
*G06K 9/00* (2006.01)
(52) U.S. Cl. ........................................ 382/131; 382/132
(58) Field of Classification Search .................. 382/128, 382/131, 132
See application file for complete search history.

(56) References Cited

U.S. PATENT DOCUMENTS

| | | |
|---|---|---|
| 6,687,528 B2 | 2/2004 | Gupta et al. |
| 6,718,055 B1 | 4/2004 | Suri |

FOREIGN PATENT DOCUMENTS

WO WO 2006086845 A1 8/2006

OTHER PUBLICATIONS

M. Hemmendorff, M. Andersson, H. Knutsson; "Phase-based Image Motion Estimation and Registration", ICASSP '99, Phoenix, AZ, USA, Mar. 1999; Others.
Y. Zhuang, Y. Rui, T.S. Huang, S. Metrotra, "Adaptive key frame extraction using unsupervised clustering", IEEE-Proceedings; Image Processing 1998 (ICIP 98), pp. 866-870; Others.
German Office Action Issued May 14, 2008.
German Search Report, May 2006.

*Primary Examiner* — Jurie Yun
(74) *Attorney, Agent, or Firm* — Harness, Dickey & Pierce, P.L.C.

(57) ABSTRACT

A method is disclosed for detecting movements and correcting movements in tomographic and projective image series. Further, a tomography or projection system is further disclosed for implementing this method. In at least one embodiment, the temporal changes in an image series with a multiplicity of temporally subsequent image data records are determined and a transformation function for correcting movements is calculated using registration methods, by which movements can be eliminated. To this end, in at least one embodiment a motion detection algorithm recognizes and distinguishes scan volumes and times at which a movement or no movement occurs. Subsequently, in at least one embodiment an algorithm for correcting the movement in those scan volumes in which a movement was detected is implemented, with the correction referring to respectively representative image intervals.

25 Claims, 4 Drawing Sheets

METHOD FOR DETECTING MOVEMENTS AND CORRECTING MOVEMENTS IN TOMOGRAPHIC AND PROJECTIVE IMAGE SERIES AND TOMOGRAPHY OR PROJECTION SYSTEM FOR IMPLEMENTING THIS METHOD

PRIORITY STATEMENT

The present application hereby claims priority under 35 U.S.C. §119 on German patent application number DE 10 2007 046 579.5 filed Sep. 27, 2007, the entire contents of which is hereby incorporated herein by reference.

FIELD

Embodiments of the invention generally relate to a method for detecting movements and correcting movements in tomographic and projective image series and/or to a tomography or projection system for implementing this method. In at least one embodiment, the temporal changes in an image series with a multiplicity of temporally subsequent image data records are determined and a transformation function is calculated using registration methods, by which movements can be eliminated.

BACKGROUND

A multiplicity of applications in medical image processing require image data to be registered as a necessary algorithmic method step. In the process, a movement of the patient due to illness, pain, breathing or another natural movement can lead to artifacts in the displayed image; in particular, a movement of the patient leads to the recorded organs no longer being imaged on the same pixels or voxels, that is to say they are no longer at the same location in an image. Such movements constitute a major problem when calculating perfusion measurements, in which the through-flow of the contrast agent per unit time must be traced as precisely as possible for each voxel in an image data record.

In order to establish a reliable perfusion measurement, a technique for motion detection and correction in time sequences has to be established. A simple known possibility is visual estimation and the removal of images which reproduce times at which a movement occurs. Subsequently only the remaining images are used to calculate the perfusion parameters.

Until now, the prior art has only published little work regarding highly developed and automated methods. In the document WO 2006/086 845 A1, Yang et al. describe a method for examining movements in perfusion time sequences. In this case, the average intensity value of a selected region of interest is plotted against time. The resultant curve is smoothed, and the differences between the plotted data points and the curve are measured. Local minima and maxima of the difference curve are detected in this manner and the interpolation is used to minimize motion artifacts. The big disadvantage of this method is that the average signal is related to motion detection rather than the congruence of voxels. Furthermore, the movement is compensated for by interpolation rather than registration, as a result of which the method is not accurate enough for calculating perfusion parameters.

The document by M. Hemmendorff, M. Andersson, H. Knutsson, "Phase-based Image Motion Estimation and Registration", ICASSP '99, Phoenix, Ariz., USA, March 1999, is also known. Here, movement compensation by quadratic filters combined with parameter models is presented for movement compensation relating to angiography data. Although this approach is very interesting, the complexity of this model seems to preclude it from repeated application relating to a perfusion measurement due to a lack of efficiency.

A method for recording MR relaxation time series with a low signal was disclosed in the document U.S. Pat. No. 6,687,528 by Gupta et al. High-contrast anatomical images are reconstructed in this method in addition to relaxation time images. The registered data of the continuous high-contrast images are subsequently transferred to the noisy relaxation time images.

In the patent specification U.S. Pat. No. 6,718,055, Suri et al. use a mutual information technique, that is to say transinformation, based on estimating Parzen windows to calculate the temporal perfusion images. However, the inventors do not subsequently analyze the time series to optimize the recording process.

Furthermore, reference is made to the document by Zhuang et al., "Adaptive key frame extraction using unsupervised clustering", IEEE-Proceedings, Image Processing 1998 (ICIP 98), pp. 866-870. This document discloses subdividing an image series into intervals using a color-related threshold algorithm and selecting appropriate key frames or interval reference comparison image data records. However, no transformation function between the reference image comparison data records, and hence between the intervals, is calculated to correct the movement; rather the key frames are used for video abstraction and summarization.

SUMMARY

In at least one embodiment of the invention, an improved automated method is disclosed for detecting and correcting movements in tomographic and projective image series. In addition, in at least one embodiment it is intended that a tomography system or projection system be introduced to implement this method.

According to the new realization of the inventors, this document presents a method for motion detection and correction. In at least one embodiment, this method is based on a motion detection algorithm which recognizes scan volumes and times at which a movement occurs, and scan volumes and times at which no movement occurs. Subsequently, an algorithm is used for correcting the movement in those scan volumes in which a movement was detected.

Overview of the motion detection algorithm:

It starts with the first data record and implements the time sequences as follows:

a. The first data record forms the start of the first interval without movement.

b. The second data record forms the subsequent data record.

c. Determining the similarity between the first and second data records. For this purpose, a difference coefficient has to be calculated which takes into account voxels whose intensity lies within given bounds. The bounds can be fixed as a function of the body part examined. For example, the values for the head can detect large parts of the skull and the jaw bones. It is also possible to use only a proportion of the voxels for motion detection to improve the computational speed. For example, it is possible to consider only every second slice image or every third voxel. Different methods known per se can be used to calculate the similarity of compared image data records for motion detection. The following methods are mentioned in an exemplary manner:
summing the square of the differences;
cross-correlation;
mutual information (MI) or normalized mutual information (NMI).

In this case, the sign of the similarity function can change. A low value means high correlation, that is to say similarity, between the data records, and a high value means a disparity between the two data records in those cases where movements occur. In the following text, this value is called the degree of disparity.

d. If the calculated degree of disparity in the case of movement exceeds a preset threshold, a new interval is created for the subsequent data record, and after this moment the interval without movement, from the last data record to the beginning of the new data record, is added to a list. If the calculated degree of disparity is below the threshold, the reference data record persists. In both cases, the subsequent data record must then be shifted to the next one.

e. The steps c and d are repeated until the end of the sequence is reached.

This provides a sequence of intervals during which no movement occurs.

Overview of the motion correction algorithm:
Based on those intervals resulting from the motion detection, the movement is corrected by registration in the following manner:

a. It is necessary to set one interval in which no movement occurs as a reference interval. It is preferable to use the longest interval, but factors such as the acquisition time can also be taken into account.

b. One data record of each interval must be marked as a reference. The middle data record of the interval is a good choice because it has the smallest probability of movement, and related artifacts, occurring. Nevertheless, in this context, a different selection is also possible. Marking the reference interval provides the global reference data record for the registration.

c. Only the reference data record of each interval is registered to the global reference data record by means of one of the known registration methods, for example by using any rigid or non-rigid registration algorithm.

d. In principle, there are two possibilities for the next step:
  i. The calculated transformation is considered to be the registration transformation for each data record of the interval without, or with small amounts of, movement.
  ii. The calculated transformation is considered to be the original transformation for initializing the registration algorithm for each data record of the interval. This results in a reduction of the calculation time if the original transformation is very close to the optimum solution.

e. The registration transformation for each data record of the interval can then be used for recalculating the registered data record by resampling in order to obtain new, movement-corrected images.

In addition, after the motion correction, it is once again possible to detect movements in the newly recorded images. By way of example, the time at which the movement occurs can be marked and displayed to the user as a critical moment. The user can then decide whether or not the images are to be kept for further calculations. This results in an improved quality of the subsequent perfusion calculation.

Using the described methods it is possible to detect and correct movements within a time sequence of images or volumes. The motion correction can be accelerated by using the information from the motion detection. In addition, critical times when movements occur can be automatically detected and marked, for example to show them to the user. The combined method of motion detection and correction permits a reliable perfusion calculation.

According to this basic idea described above, in at least one embodiment, the inventors propose a method for detecting movements in tomographic or projective image series, comprising the following method steps:

1—generating a time series of tomographic or projective image data records of an examination object,
2—determining a first image data record as reference comparison image data record,
3—determining a threshold value, exceeding which is intended to be considered a movement,
4—selecting a second image data record which is temporally subsequent to the first image data record as a comparison image data record,
5—calculating a degree of disparity between the reference comparison image data record and the comparison image data record, at least with respect to a predetermined subsection,
6—if the degree of disparity lies above the fixed threshold value: defining the start of the new image interval and using the comparison image data record as the new reference comparison image data record, otherwise assigning the comparison image data record to the current image interval,
7—selecting a temporally subsequent image data record as a new comparison image data record until the end of the image series is reached,
8—if a new, temporally subsequent comparison image data record is present: continuing the method with step 5,
9—selecting an image interval as a representative image interval,
10—selecting respectively one image data record from each image interval as interval reference comparison image data record,
11—determining a transformation function for each image interval based on the spatial differences between the interval reference comparison image data record of the representative image interval and every other interval reference comparison image data record,
12—correcting the image data records from the image intervals using the previously determined interval-specific transformation functions and
13—outputting the corrected image data records for further processing and/or displaying the corrected image data records.

Thus, in accordance with the procedure described above, the image data records are assigned to individual image intervals with similar voxel-by-voxel positioning and are "aligned" with one another, image interval-by-image interval, with respect to the position of the anatomical structures, such that very precise spatial comparisons are possible over an extended period of time. By way of example, in this manner, the perfusion can be measured very precisely even over relatively long times, without losing significance. Furthermore, the required basic calculation for alignment is only implemented once in the case of relatively long image intervals with similar positioning and is applied to all image data records of the respective image interval.

It can be advantageous if the associated interval-specific transformation function is applied to each image data record to be corrected for correction in accordance with step 12. Alternatively, for correction, it is also possible that every image data record to be corrected is registered individually by applying the respectively interval-specific transformation function as the initial transformation for the registration process.

If the computational time is intended to be optimized, the degree of disparity can be calculated only for a part of the present image data, for example only for every n-th voxel or every m-th slice image, it preferably being possible for n or m to assume values between 2 and 8 inclusive. Combinations of this are also possible.

The degree of disparity for determining movement present can be calculated by statistical methods known per se, for example by summing the absolute difference or the square of the difference, or by calculating a cross-correlation coefficient, of voxel values of in each case two image data records. It is also possible to form the degree of disparity by calculating the mutual information (MI) or the normalized mutual information (NMI) of voxel values of in each case two image data records. In this process, it is also advantageous if only voxels within a preset value range are used to calculate the degree of disparity.

A possible method for selecting the representative image interval in accordance with step 9 can consist of using the longest image interval occurring in the time series.

Furthermore, it can be expedient if the image data record located in the middle of the respective interval with respect to time is selected as the interval reference image data record in accordance with method step 10.

By way of example, according to at least one embodiment of the invention, it is possible to use for the method described above tomographic image data records from an x-ray computed tomography examination, from a magnetic resonance imaging examination, from a positron emission tomography examination or from an ultrasound examination. However, the method according to the invention is not only related to tomographic data, but it can also be applied to image data records from projective examination systems, such as x-ray fluoroscopy systems.

It is furthermore within the scope of at least one embodiment of the invention that, when outputting the tomographic or projective image data records, the already calculated associated degrees of disparity of the original image data records are displayed as movement information. Alternatively, or additionally, it is also possible for the newly calculated associated degrees of disparity of the corrected image data records to be displayed as information regarding remaining movements that cannot be corrected. It is furthermore possible to display interval associations.

In accordance with at least one embodiment of the method described above, the inventors also propose an imaging system for generating a multiplicity of temporally sorted tomographic or projective image data records comprising a computational and control unit with a program memory and programs for controlling the imaging system and for calculating image data, in which, according to at least one embodiment of the invention, program code is also intended to be saved in the program memory which implements the method steps according to at least one embodiment of the invention when executed on the control and computational unit.

By using the method described above, it is now possible to implement motion detection and motion correction within a time sequence of image data records. The motion correction can additionally be accelerated by using information from the motion detection. Additionally, it is possible to automatically detect and mark critical times where movements occur to display critical time periods to the user. Overall, the combined method for motion detection and motion correction permits a very reliable perfusion calculation.

BRIEF DESCRIPTION OF THE DRAWINGS

In the following text, embodiments of the invention are described in more detail with aid of the figures, in which only the features required to understand the invention are illustrated. In this case, the following reference symbols are used: 1: x-ray CT system, 2: first x-ray tube, 3: first detector, 4: second x-ray tube (optional), 5: second detector (optional), 6: gantry housing, 7: patient, 8: patient couch, 9: system axis, 10: control and computational unit, 11: profile of the degrees of disparity, 12: threshold value, BI2, BI3: movement interval, B0-B19: image data records, I1-I3: image intervals, T1-T3: transformations, $Prg_1$-$Prg_n$: computer programs.

In detail.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
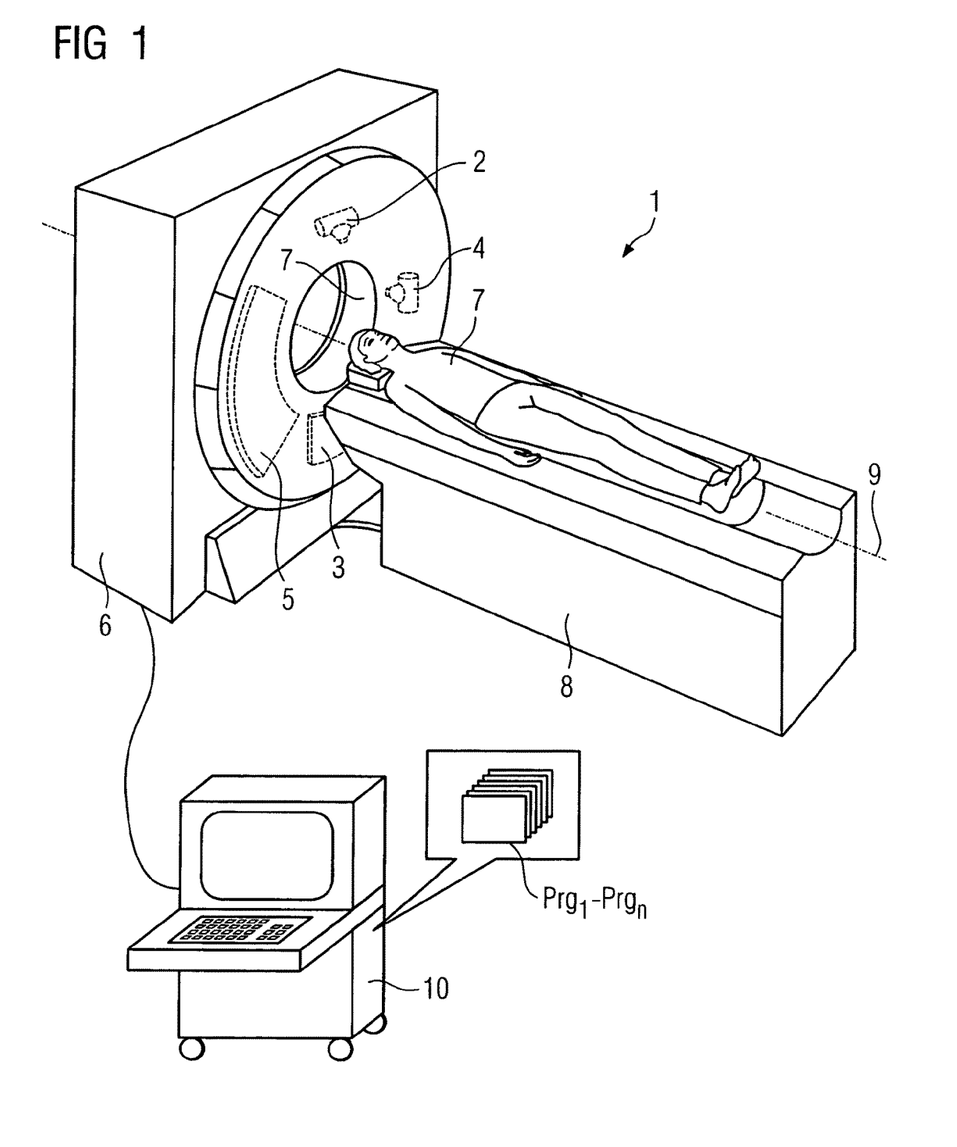
FIG. 1 shows an x-ray computed tomography system designed to implement the method according to an embodiment of the invention.

FIG. 1 shows as an example of a tomography system an x-ray CT system 1 designed to implement the method according to an embodiment of the invention. The CT system 1 has a gantry housing 6, with a first x-ray tube 2 with a detector 3 lying opposite it, and an optional second x-ray tube 4 with a likewise optional detector 5 lying opposite it. A patient 7 can be pushed into a measurement field between the x-ray tubes and the detectors along a z-axis 9 using a displaceable patient couch 8. For the purposes of scanning the patient 7, the patient can either be kept in a specific scanning position or be moved, so that a particular region of the patient 7 is scanned for an extended period of time. This makes it possible for the perfusion to be measured in certain areas if contrast agents are supplied at the same time. For this purpose, it is necessary to be able to determine the spread of this contrast agent later, in high spatial resolution, with the spatial comparison being intended to relate to the patient-specific or organ-specific coordinate system. Due to breathing movements, heart movements or any other intended or unintended movements of the patient, this usually results in relative displacements between the well-defined coordinate system of the patient table and the organs, so that these relative displacements have to be corrected for a precise perfusion measurement.

FIG. 1 also shows a control and computational unit 10 which comprises a memory which holds programs $Prg_1$ to $Prg_n$, by means of which the system is controlled and the data is evaluated. At least one of these programs $Prg_1$ to $Prg_n$ also implements the previously described method according to the invention when executed. Optionally, it is possible to load further programs or program modules, which can likewise implement the variants according to an embodiment of the invention of the previously described method.

Figure 2:
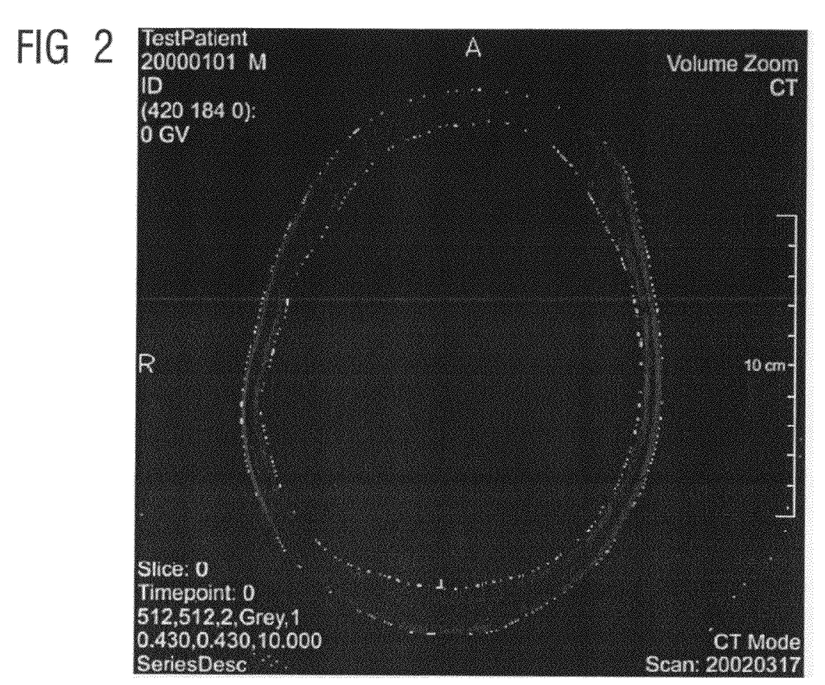
FIG. 2 shows an image of the squares of the differences between two cranial slice image data records with a small amount of movement.
Figure 3:
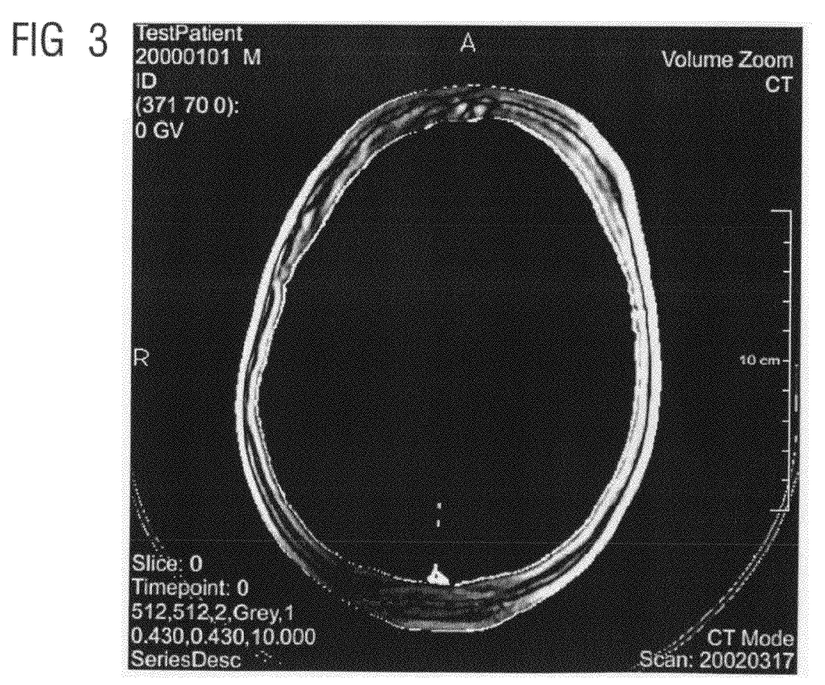
FIG. 3 shows an image of the squares of the differences between two cranial slice image data records with a large amount of movement.

FIGS. 2 and 3 show difference-squared slice images of a head, with FIG. 2 originating from two image data records between which there is little movement, while the difference-squared slice image of FIG. 3 originates from two image data records of a movement phase. The magnitude of the square of the difference of each pixel is in this case rendered as a grayscale value, so that an image which is as black as possible shows no movement, and a light image shows large amounts of movement.

Figure 4:
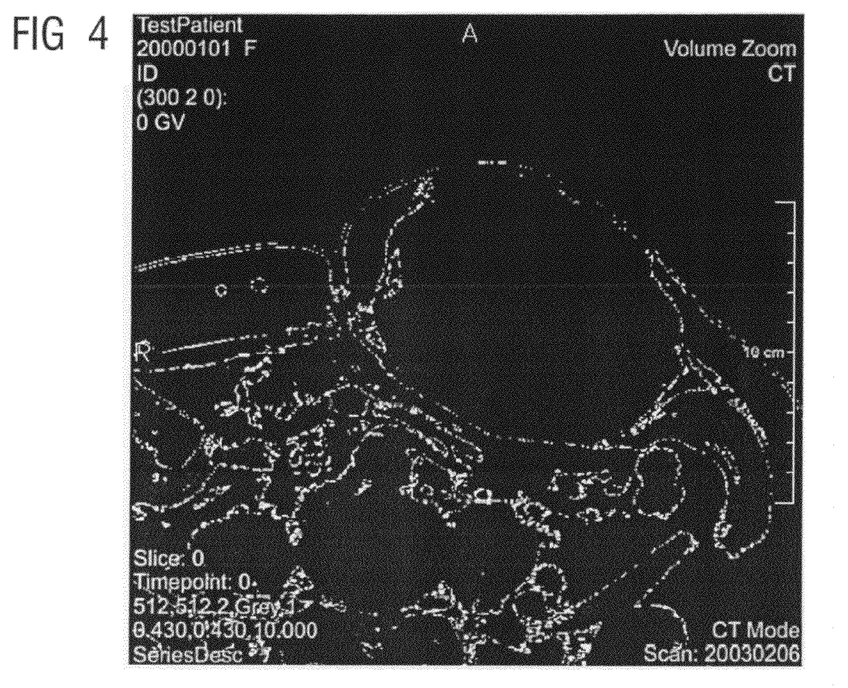
FIG. 4 shows an image of the squares of the differences between two slice image data records of a cardiac malignant melanoma with a small amount of movement.
Figure 5:
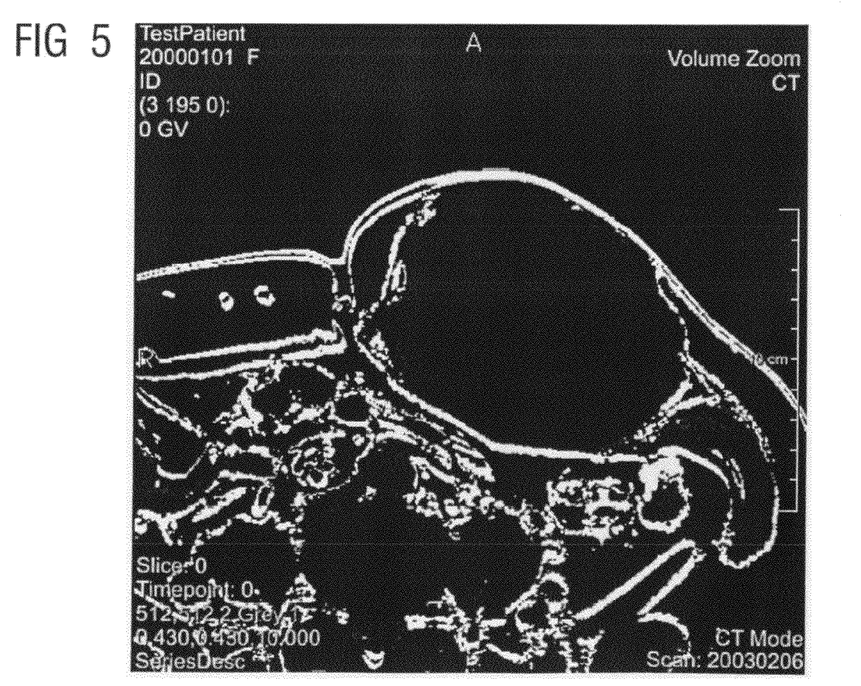
FIG. 5 shows an image of the squares of the differences between two slice image data records of a cardiac malignant melanoma with a large amount of movement.

FIGS. 4 and 5 likewise show difference-squared slice images; however in this case they show images of a heart with a malignant melanoma. In this case too, the image of FIG. 4 shows a situation with very little movement, whereas the slice image of FIG. 5 renders large amounts of movement.

If the squares of the differences shown in FIGS. 2 to 5 are summed over the whole image and, if applicable, normalized with regard to the number of pixels considered, a so-called degree of disparity can be specified for each image or each considered image time.

In this context, reference should be made to the fact that other calculation variants are also possible, such as the mutual information (MI) or normalized mutual information (NMI) present between two images. It is likewise possible to calculate a cross-correlation coefficient or even only simple absolute values of the degree of disparity. What is essential is that the computational scheme used represents a measure for the similarity of the two images.

Figure 6:
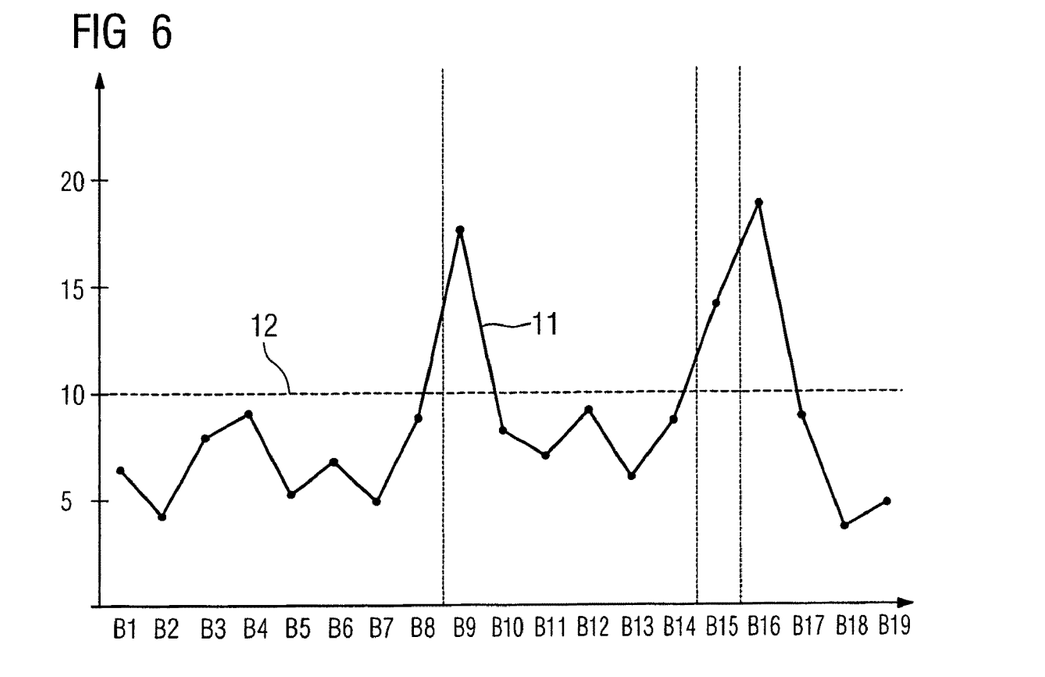
FIG. 6 shows degrees of disparity in a series of image data records.

FIG. 6 shows a graph, in which such degrees of disparity are plotted on the ordinate against time or a continuous numbering of image data records B1 to B19, recorded one after another, on the abscissa. It can be seen from the profile of the curve 11 that there are image data records whose degrees of disparity are below a plotted threshold value 12, although this threshold value is occasionally exceeded. In this case, this occurs at the image data records numbered B9, B15 and B16. According to the invention, a new image interval is initiated with each of these image data records, and the preceding interval also ends here. Thus, four image intervals B1 to B8, B9 to B14, B15, and B16 to B19 are shown in FIG. 6. As an extreme case, it is thus also possible that an image interval consists of a single image data record—in this case this applies to the third interval at B15. According to the invention, all image data records of an image interval are treated the same with respect to their transformation, so that, as a matter of fact, the transformation function also only has to be calculated once per image interval. This leads to significant time-saving.

Figure 7:
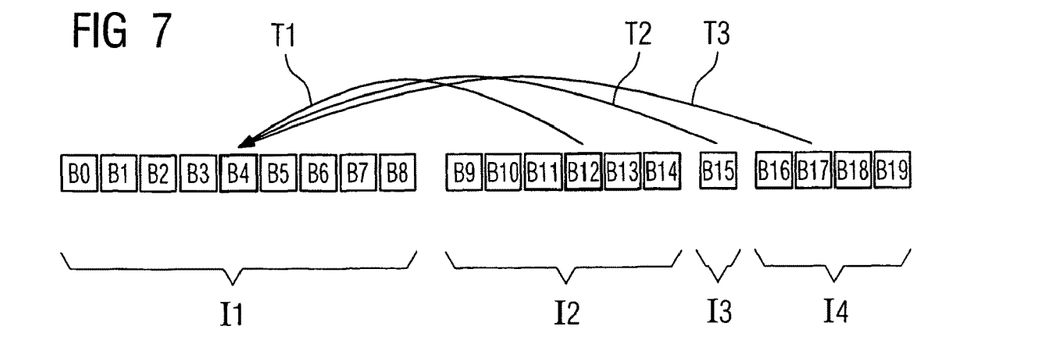
FIG. 7 shows a schematic illustration of the image intervals with transformations applied according to an embodiment of the invention.

This system is illustrated again in FIG. 7 in a different manner. The boxes with the numbers B0 to B19 represent the image data records. These image data records are displayed in groups in individual image intervals I1 to I4 according to the findings of FIG. 6. The image interval I1 additionally comprises the first image B0, in which the difference measurement was initiated and so no degree of disparity is plotted for this image in FIG. 6. Image interval I1 was chosen as the representative image interval due to its length, and the image data records of the image intervals I2 to I4 are now registered with respect to this by applying a common transformation function to each image interval. The transformations are described by the arrows T1 to T3.

Accordingly it is thus possible to find transformation functions, in this case T1 to T3, which are based on registered differences between the representative image data record and the reference image data records of the individual image intervals, and are used to transform the image data records from the different image intervals onto the representative image data record.

If the transformed image data records are present, they can be output for visual evaluation or can be passed on for further processing, such as for perfusion calculations, or be further processed.

It is understood that the features of the invention mentioned above can be used not only in the respectively specified combination but also in other combinations or on their own without leaving the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for detecting and correcting movements in tomographic or projective image series, comprising:
generating a time series of tomographic or projective image data records of an examination object;
determining a first image data record as a reference comparison image data record;
determining a threshold value, wherein exceeding the threshold value is intended to be considered a movement;
selecting a second image data record, temporally subsequent to the first image data record, as a comparison image data record;
calculating a degree of disparity between the reference comparison image data record and the comparison image data record, at least with respect to a subsection;
defining a start of a new image interval if the degree of disparity lies above the threshold value and using the comparison image data record as a new reference comparison image data record, and assigning the comparison image data record to a current image interval if the degree of disparity does not lie above the threshold value;
selecting a temporally subsequent image data record as a new comparison image data record until an end of the image series is reached;
repeating the calculating, defining and selecting of a temporally subsequent image data record if a new, temporally subsequent comparison image data record is present;
selecting an image interval as a representative image interval;
selecting respectively one image data record from each image interval as an interval reference comparison image data record;
determining a transformation function for correcting movements for each image interval based on spatial differences between the interval reference comparison image data record of the representative image interval and every other interval reference comparison image data record;
correcting image data records from the image intervals using the determined transformation functions; and
at least one of outputting the corrected image data records for further processing and displaying the corrected image data records.

2. The method as claimed in claim 1, wherein a transformation function is applied to each image data record to be corrected.

3. The method as claimed in claim 1, wherein, for the correcting, every image data record to be corrected is registered individually by applying a respective transformation function as an initial transformation for a registration process.

4. The method as claimed in claim 1, wherein the degree of disparity is only calculated for every n-th voxel.

5. The method as claimed in claim 4, wherein n assumes a value between 2 and 8 inclusive.

6. The method as claimed in claim 1, wherein the degree of disparity is calculated only for every m-th slice image.

7. The method as claimed in claim 6, wherein m assumes a value between 2 and 8 inclusive.

8. The method as claimed in claim 1, wherein the degree of disparity is calculated by summing an absolute difference of voxel values of, in each case, two image data records.

9. The method as claimed in claim 1, wherein the degree of disparity is calculated by summing a square of a difference between voxel values of, in each case, two image data records.

10. The method as claimed in claim 1, wherein the degree of disparity is calculated by calculating a cross-correlation coefficient of voxel values of, in each case, two image data records.

11. The method as claimed in claim 1, wherein the degree of disparity is formed by calculating a mutual information of voxel values of, in each case, two image data records.

12. The method as claimed in claim 1, wherein the degree of disparity is formed by calculating a normalized, mutual information of voxel values of, in each case, two image data records.

13. The method as claimed in claim 1, wherein only voxels within a preset value range are used to calculate the degree of disparity.

14. The method as claimed in claim 1, wherein a longest image interval occurring in the time series is selected as the representative image interval.

15. The method as claimed in claim 1, wherein the image data record located in the middle of the respective interval with respect to time is selected as the interval reference comparison image data record.

16. The method as claimed in claim 1, wherein tomographic image data records from an x-ray computed tomography examination are used.

17. The method as claimed in claim 1, wherein tomographic image data records from a magnetic resonance imaging examination are used.

18. The method as claimed in claim 1, wherein tomographic image data records from a positron emission tomography examination are used.

19. The method as claimed in claim 1, wherein projective image data records from an x-ray examination are used.

20. The method as claimed in claim 1, wherein projective image data records from an ultrasound examination are used.

21. The method as claimed in claim 1, wherein, when outputting the tomographic or projective image data records, the calculated associated degrees of disparity of original image data records are displayed as movement information.

22. The method as claimed in claim 1, wherein, when outputting the tomographic or projective image data records, newly calculated associated degrees of disparity of the corrected image data records are displayed as information regarding remaining movements that cannot be corrected.

23. The method as claimed in claim 1, wherein interval associations are displayed when outputting the tomographic or projective image data records.

24. An imaging system for generating a multiplicity of temporally sorted tomographic or projective image data records, comprising:
a computational and control unit including a program memory and programs for controlling the imaging system and for calculating image data, wherein program code saved in the program memory implements the method of claim 1 when executed on the control and computational unit.

25. A non-transitory computer readable medium including program segments for, when executed on a computer device, causing the computer device to implement the method of claim 1.

* * * * *